United States Patent
Tong et al.

(10) Patent No.: US 7,309,642 B2
(45) Date of Patent: Dec. 18, 2007

(54) METALLIC QUANTUM DOTS FABRICATED BY A SUPERLATTICE STRUCTURE

(75) Inventors: William M. Tong, San Francisco, CA (US); M. Saif Islam, Sacramento, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 11/271,354

(22) Filed: Nov. 9, 2005

(65) Prior Publication Data

US 2007/0105353 A1 May 10, 2007

(51) Int. Cl.
*H01L 21/30* (2006.01)
*H01L 21/46* (2006.01)

(52) U.S. Cl. .................. 438/458; 977/888; 977/893

(58) Field of Classification Search ............... 438/458; 977/888, 893
See application file for complete search history.

(56) References Cited

U.S. PATENT DOCUMENTS

| | | | |
|---|---|---|---|
| 5,614,435 A * | 3/1997 | Petroff et al. | ........... 117/85 |
| 5,747,180 A * | 5/1998 | Miller et al. | ........... 428/601 |
| 5,965,212 A | 10/1999 | Dobson et al. | |
| 6,294,450 B1 | 9/2001 | Chen et al. | |
| 6,407,443 B2 | 6/2002 | Chen et al. | |
| 6,518,189 B1 | 2/2003 | Chou | |
| 6,518,194 B2 | 2/2003 | Winningham et al. | |
| 6,774,014 B1 | 8/2004 | Lee et al. | |
| 6,809,356 B2 | 10/2004 | Chou | |
| 6,828,244 B2 | 12/2004 | Chou | |
| 2004/0079278 A1 | 4/2004 | Kamins et al. | |
| 2005/0218394 A1 | 10/2005 | Schmid et al. | |
| 2005/0250276 A1* | 11/2005 | Heath et al. | ........... 438/200 |
| 2006/0164634 A1 | 7/2006 | Kamins et al. | |
| 2006/0209300 A1 | 9/2006 | Kamins et al. | |

FOREIGN PATENT DOCUMENTS

WO   WO01/84238   11/2001
WO   WO 2004012234 A2 *   2/2004

OTHER PUBLICATIONS

Melosh, Nicholas A., et al., "Ultrahigh-Density Nanowire Lattices and Circuits," Science, vol. 300, Apr. 4, 2003, pp. 112-115.
Lindberg V et al—"Metallic Quantum Dots"—Journal of Physics: Condensed Matter—vol. 17 No. 13—Apr. 6, 2005—pp. S1075-S1094.
Liang, Jianyu et a—"Two-dimensional Lateral Superlattices of Nanostructures: Nonlithographic Formation by Anodic Membrane Template"—Journ of Appl Phys—vol. 91 No. 4—Feb. 15, 2002.

* cited by examiner

*Primary Examiner*—David W. Coleman

(57) ABSTRACT

A method for forming quantum dots includes forming a superlattice structure that includes at least one nanostrip protruding from the superlattice structure, providing a quantum dot substrate, transferring the at least one nanostrip to the quantum dot substrate, and removing at least a portion of the at least one nanostrip from the substrate. The superlattice structure is formed by providing a superlattice substrate, forming alternating layers of first and second materials on the substrate to form a stack, cleaving the stack to expose the alternating layers, and etching the exposed alternating layers with an etchant that etches the second material at a greater rate than the first to form the at least one nanostrip.

20 Claims, 7 Drawing Sheets

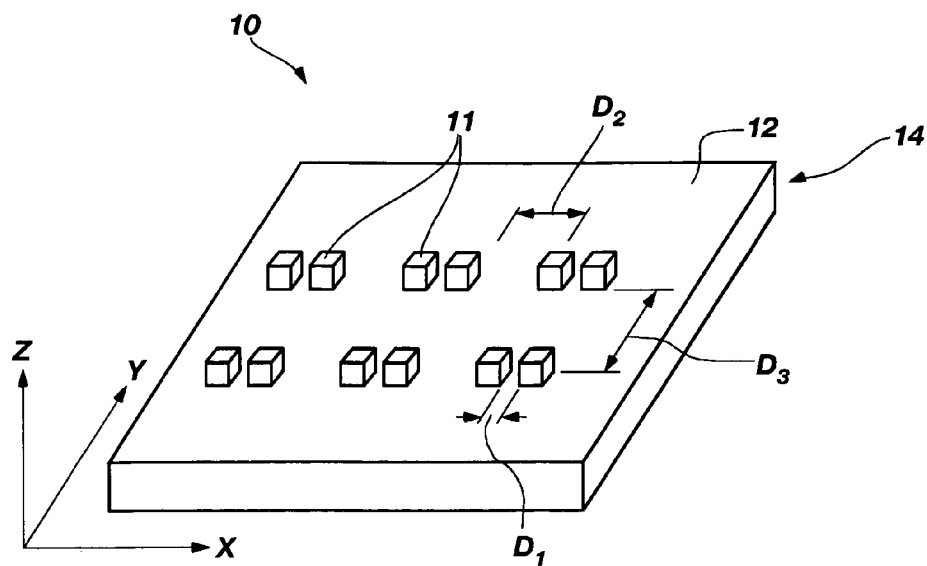
FIG. 1
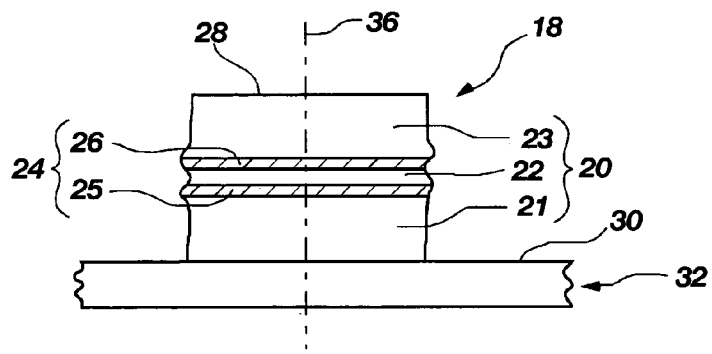
FIG. 2A
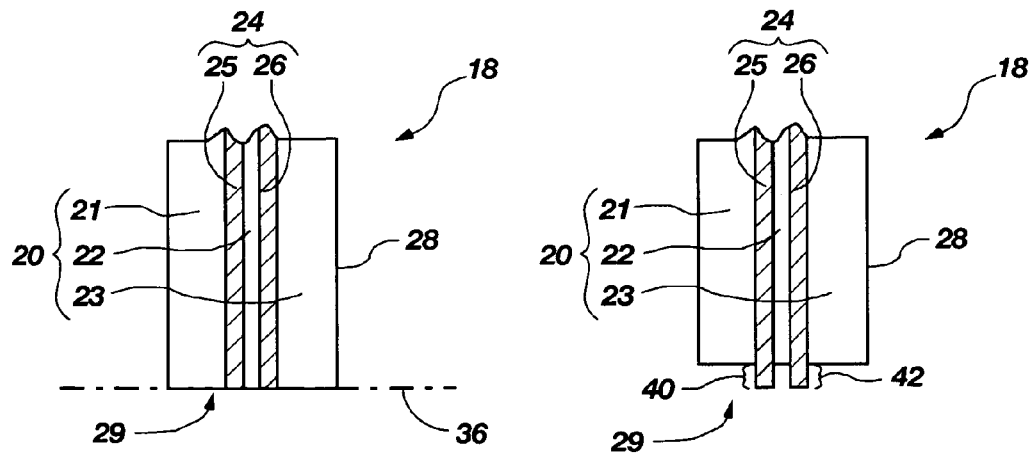
FIG. 2B     FIG. 2C

METALLIC QUANTUM DOTS FABRICATED BY A SUPERLATTICE STRUCTURE

FIELD OF THE INVENTION

The present invention relates to methods for forming quantum dots on the surface of a substrate. More particularly, the invention relates to methods for forming a plurality of metallic quantum dots on the surface of a substrate, methods for forming NERS-active structures that include at least two quantum dots, and methods for performing NERS using such NERS-active structures.

BACKGROUND OF THE INVENTION

Quantum dots are small particles of matter that typically have cross-sectional dimensions of less than about ten nanometers. Quantum dots generally are small enough that the addition of an electron to the quantum dot or the removal of an electron from the quantum dot changes the properties of the quantum dot in some detectable way. Quantum dots have been employed in several areas of technology. For example, quantum dots have been used in lasers, light emitting diodes and infrared detectors. Extensive research is currently being conducted to identify additional applications for quantum dots in these areas of technology, and to determine the utility of quantum dots in other areas of technology including electronics, optoelectronics, telecommunications, and biotechnology.

The performance or behavior of a device that includes quantum dots generally is at least partially dependent upon the size and shape of the individual quantum dots, and upon the spacing between the quantum dots. Therefore, the ability to produce a useful and functional device that employs quantum dots is at least partially a function of the ability to produce quantum dots having well controlled size, shape, and spacing. It may be desirable or necessary to control the size, shape and spacing to within a few nanometers. These extremely small dimensions and extremely tight tolerance requirements make the production of quantum dots very difficult.

Various techniques and methods for producing quantum dots have been presented in the art. Such techniques include chemical synthesis, molecular beam epitaxy, chemical vapor deposition, and gas condensation techniques, such as thermal evaporation, sputtering, electron beam evaporation, or laser ablation. Self-assembly techniques have also been employed to produce quantum dots.

These techniques for producing quantum dots that have been presented in the art generally suffer from at least one of two problems. First, many techniques cannot control the size, shape, and spacing of the quantum dots in a sufficiently precise manner. Second, many techniques are slow or expensive and, therefore, are not economically suitable for mass producing quantum dots or devices that include quantum dots. As a result, there is a need in the art for methods that allow for the production of quantum dots having well controlled size, shape, and spacing. Furthermore, there is a need in the art for methods that facilitate the mass production of such quantum dots in an economically efficient manner.

One area of technology in which quantum dots may be employed is nano-enhanced Raman spectroscopy (NERS).

Raman spectroscopy is a well-known technique for analyzing molecules or materials. In conventional Raman spectroscopy, high intensity monochromatic radiation provided by a radiation source, such as a laser, is directed onto an analyte (or sample) that is to be analyzed. This radiation may be referred to as the incident radiation. In Raman spectroscopy, the wavelength of the incident radiation typically is varied over a range of wavelengths within or near the visible region of the electromagnetic spectrum. A majority of the photons of the incident radiation are elastically scattered by the analyte. In other words, the scattered photons have the same energy, and thus the same wavelength, as the incident photons. However, a very small fraction of the photons are inelastically scattered by the analyte. Typically, only about 1 in $10^7$ of the incident photons are inelastically scattered by the analyte in conventional Raman spectroscopy. These inelastically scattered photons have a different wavelength than the incident photons. This inelastic scattering of photons is termed "Raman scattering". The Raman scattered photons can have wavelengths less than, or, more typically, greater than the wavelength of the incident photons.

When an incident photon collides with the analyte, energy can be transferred from the photon to the molecules or atoms of the analyte, or from the molecules or atoms of the analyte to the photon. When energy is transferred from the incident photon to the analyte, the Raman scattered photon will have a lower energy and a corresponding longer wavelength than the incident photon. These Raman scattered photons having lower energy than the incident photons are collectively referred to in Raman spectroscopy as the "Stokes radiation." A small fraction of the analyte molecules or atoms can be in an energetically excited state when photons are incident thereon. When energy is transferred from the analyte to the incident photon, the Raman scattered photon will have a higher energy and a corresponding shorter wavelength than the incident photon. These Raman scattered photons having higher energy than the incident photons are commonly referred to in Raman spectroscopy as the "anti-Stokes radiation." The Stokes radiation and the anti-Stokes radiation collectively are referred to as the Raman scattered radiation or the Raman signal.

The Raman scattered radiation is detected by a detector that typically includes a wavelength-dispersive spectrometer and a photomultiplier for converting the energy of the impinging photons into an electrical signal. The characteristics of the electrical signal are at least partially a function of both the energy of the Raman scattered photons as evidenced by their wavelength, frequency, or wave number, and the number of the Raman scattered photons as evidenced by the intensity of the Raman scattered radiation. The electrical signal generated by the detector can be used to produce a spectral graph illustrating the intensity of the Raman scattered radiation as a function of the wavelength of the Raman scattered radiation. Analyte molecules and materials generate unique Raman spectral graphs. The unique Raman spectral graph obtained by performing Raman spectroscopy can be used for many purposes including identification of an unknown analyte, or determination of physical and chemical characteristics of a known analyte.

Raman scattering of photons is a weak process. As a result, powerful, costly laser sources typically are used to generate high intensity incident radiation to increase the intensity of the weak Raman scattered radiation for detection. Surface-enhanced Raman spectroscopy (SERS) is a technique that has been developed to enhance the intensity of the Raman scattered radiation relative to conventional Raman spectroscopy. In SERS, the analyte molecules typically are adsorbed onto or placed adjacent to what has been referred to as a SERS-active structure. SERS-active structures typically include a metal surface or structure. Interactions between the analyte and the metal surface cause an increase in the intensity of the Raman scattered radiation. The mechanism by which the intensity of the Raman scattered radiation is enhanced is not completely understood. Two main theories of enhancement mechanisms have been presented in the literature: electromagnetic enhancement and chemical enhancement.

Several types of metallic structures have been employed in SERS techniques to enhance the intensity of Raman scattered radiation that is scattered by analyte molecules adjacent thereto. Some examples of such structures include electrodes in electrolytic cells, metal colloid solutions, and metal substrates such as a roughened metal surface. For example, it has been shown that adsorbing analyte molecules onto or near a specially roughened metal surface made from gold or silver can enhance the Raman scattering intensity by factors of between $10^3$ and $10^6$.

Recently, Raman spectroscopy has been performed employing randomly oriented nanostructures, such as nanometer scale needles, particles, and wires, as opposed to a simple roughened metallic surface. This process will be referred to hereinafter as nano-enhanced Raman spectroscopy (NERS). The intensity of the Raman scattered photons from a molecule adsorbed proximate to nanoparticles or structures that include nanoparticles can be increased by factors as high as $10^{16}$. At this level of sensitivity, NERS has been used detect single molecules. Detecting single molecules with high sensitivity and molecular specificity is of great interest in the fields of chemistry, biology, medicine, pharmacology, and environmental science. However, it is unknown what configurations, including size, shape and spacing, of metallic nanoparticles will enhance the intensity of Raman scattered radiation most effectively. In addition, it has proven very difficult to fabricate metallic nanoparticles having well controlled size, shape and spacing.

Accordingly, there is a need for a method that can be used to quickly and cost-effectively produce quantum dots and nanoparticles having well controlled size, shape, and spacing that can be used to enhance the intensity of Raman scattered radiation scattered by an analyte in the vicinity of the quantum dots while performing NERS.

BRIEF SUMMARY OF THE INVENTION

The present invention relates to methods for forming quantum dots on the surface of a substrate. According to one aspect of the present invention, a method for forming at least two quantum dots includes forming a superlattice structure having at least one nanostrip protruding therefrom, providing a quantum dot substrate, transferring the at least one nanostrip from the superlattice structure to the quantum dot substrate, and removing at least a portion of the at least one nanostrip from the quantum dot substrate. The superlattice structure is formed by providing a superlattice substrate, forming a plurality of alternating layers of a first material and a second material on the superlattice substrate to form a stack having a major surface parallel to that of the superlattice substrate. The second material is different from the first material. The stack is cleaved normal to the major surface to expose the plurality of alternating layers, and the exposed plurality of alternating layers are etched using an etchant that etches the first material at a greater rate than the second material to form at least one nanostrip comprising the second material that protrudes from the stack.

According to another aspect of the present invention, a method for forming a NERS-active structure includes forming a superlattice structure having at least one nanostrip protruding therefrom, providing a NERS-active structure substrate comprising an electrically insulating material, transferring the at least one nanostrip comprising the NERS-active material from the superlattice structure to a surface of the NERS-active structure substrate, and removing at least a portion of the at least one nanostrip comprising the NERS-active material from the NERS-active structure substrate to provide at least two quantum dots comprising the NERS-active material on the surface of the NERS-active structure substrate.

To form the superlattice structure, a superlattice substrate is provided, and a plurality of alternating layers of a first material and a second material are formed on the superlattice substrate to form a stack having a major surface parallel to that of the superlattice substrate. The second material includes a NERS-active material, and the first material differs from the second material. The stack is cleaved normal to the major surface to expose the plurality of alternating layers, and the exposed plurality of alternating layers are etched to a chosen depth using an etchant that etches the first material at a greater rate than the second material to form at least one nanostrip that includes the NERS-active material.

According to another aspect of the present invention, a method for performing NERS includes providing a NERS-active structure having at least two quantum dots including a NERS-active material, providing an analyte proximate the at least two quantum dots, irradiating the analyte and the at least two quantum dots, and detecting Raman scattered radiation scattered by the analyte. To provide the NERS-active structure, a superlattice structure is formed that has at least one nanostrip comprising a NERS-active material protruding therefrom. A NERS-active structure substrate comprising an electrically insulating material is provided, and the at least one nanostrip is transferred to a surface of the NERS-active structure substrate. At least a portion of the at least one nanostrip is removed from the surface of the NERS-active structure substrate to provide the at least two quantum dots comprising the NERS-active material on the surface of the NERS-active structure substrate.

The superlattice structure is formed by providing a superlattice substrate and forming a plurality of alternating layers of a first material and a second material on the superlattice substrate to form a stack having a major surface parallel to that of the superlattice substrate. The second material includes a NERS-active material, and the first material is different from the second material. The stack is cleaved normal to its major surface to expose the plurality of alternating layers, and the exposed plurality of alternating layers are etched to a chosen depth using an etchant that etches the first material at a greater rate than the NERS-active material to form the at least one nanostrip comprising the NERS-active material. The at least one nanostrip protrudes from the stack.

The features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

FIG. 1 is a perspective view of a representative embodiment of a plurality of quantum dots fabricated on the surface of a substrate that may be configured as a NERS-active structure;

FIGS. 2A-2C illustrate a representative method for forming a superlattice structure that can be used to fabricate the plurality of quantum dots shown in FIG. 1;

DETAILED DESCRIPTION OF THE INVENTION

Figure 3A:
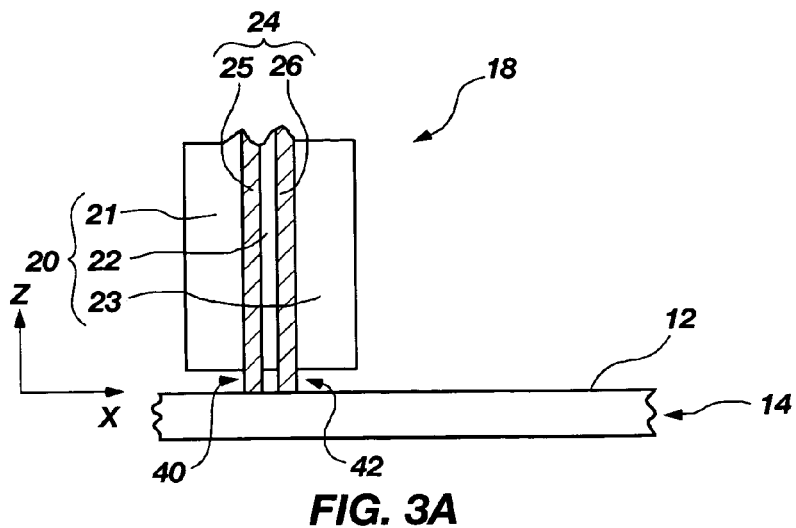
FIGS. 3A-3D illustrate a representative method for using the superlattice structure shown in FIG. 2C to fabricate an intermediate structure shown in FIG. 4 that can be used to form the plurality of quantum dots shown in FIG. 1.

The present invention relates to methods for forming quantum dots on the surface of a substrate. More particularly, the invention relates to methods for forming a plurality of metallic quantum dots on the surface of a substrate, methods for forming NERS-active structures that include at least two quantum dots, and methods for performing NERS using such NERS-active structures.

The term "NERS-active material" as used herein means a material that, when formed into nanoparticles having appropriate geometries or configurations, is capable of increasing the number of Raman scattered photons that are scattered by a molecule when the molecule is located proximate to that material and when the molecule and material are subjected to electromagnetic radiation. NERS-active materials can be used to form NERS-active structures. NERS-active materials include, but are not limited to, silver, gold, and copper.

The term "NERS-active structure" as used herein means a nanoparticle, or a structure that includes at least one nanoparticle, that is capable of increasing the number of Raman scattered photons that are scattered by a molecule when the molecule is located proximate to that nanoparticle and the molecule and structure are subjected to electromagnetic radiation.

The term "quantum dot" as used herein means a particle of any shape having at least one cross-sectional dimension of less than about 10 nanometers.

The term "nanoparticle" as used herein means a particle of any shape having at least one cross-sectional dimension of less than about 100 nanometers. Examples of nanoparticles include, but are not limited to, quantum dots, nanodots, nanowires, nanocolumns, nanospheres, and nanostrips.

The term "nanostrip" as used herein means any elongated structure having at least one cross-sectional dimension of less than about 100 nanometers.

The term "analyte" as used herein means any molecule, material, or substance that is to be analyzed by NERS.

The illustrations presented herein are not meant to be actual views of any particular embodiment of the present invention, but are merely idealized representations which are employed to describe the present invention. Additionally, elements common between figures may retain the same numerical designation.

FIG. 1 is a perspective view of a structure 10 that includes a plurality of quantum dots 11 disposed on a surface 12 of a substrate 14. Quantum dots 11, such as those shown in FIG. 1, may be used for numerous applications in various areas of technology. The desired arrangement of the quantum dots 11 may be at least partially a function of the application for which the quantum dots 11 are to be used. For example, as shown in FIG. 1, the plurality of quantum dots 11 may include twelve quantum dots 11 arranged in two rows of three pairs of quantum dots 11. The individual quantum dots 11 in each pair may be separated from one another by a distance $D_1$. Adjacent pairs of quantum dots 11 in each row may be separated from one another in an X direction by a distance $D_2$. In addition, each row of quantum dots 11 may be separated from one another in a Y direction by a distance $D_3$. It should be understood that innumerable arrangements or configurations of quantum dots 11 are possible, any one of which may be desirable depending upon the application for which the quantum dots 11 are to be used.

For purposes of illustration, the quantum dots 11 are shown in FIG. 1 to have a cubic shape. It should be understood that the quantum dots 11 may have any shape. For example, the quantum dots 11 may have a spherical, semispherical, triangular, rectangular or other polygonal shape. In addition, the quantum dots may have at least one cross-sectional dimension of less than about 10 nanometers. The quantum dots 11 may be formed from, for example, metal materials including, but not limited to, gold, silver, copper, platinum, and palladium.

An exemplary method for forming the plurality of quantum dots 11 on the surface 12 of the substrate 14 can be described with reference to FIGS. 2A-2C, 3A-3D, 4, and 5A-5C. The method, as will be described in further detail below, may include providing a superlattice structure, transferring material from the superlattice structure to the surface of a substrate to form a plurality of nanostrips thereon, and subsequently removing at least a portion of the nanostrips from the surface of the substrate.

FIGS. 2A-2C illustrate an exemplary method for forming a superlattice structure 18 that may be used to fabricate the plurality of quantum dots 11 shown in FIG. 1. The superlattice structure 18 may include a plurality of alternating first material layers 20 and second material layers 24. The first material layers 20 may include, for example, an oxide material. The second material layers 24 may include a material used to form the quantum dots 11. For example, the second material layers 24 may include gold, silver, copper, platinum, or palladium.

To form the superlattice structure 18, a first material layer 21 may be deposited on a surface 30 of a superlattice substrate 32 shown in FIG. 2A. The superlattice substrate 32 may be formed from, for example, silicon or silica. Many other materials may be suitable for use as superlattice substrate 32 and such materials also may be used. The thickness of the first material layer 21 is not critical and may be, for example, greater than about 10 nanometers. For example, the first material layer 21 may be several microns thick.

A second material layer 25 may be deposited over the first material layer 21. The thickness of one individual quantum dot 11 in each pair of quantum dots 11 shown in FIG. 1 in the X direction may be, at least partially, a function of the thickness of the second material layer 25. Therefore, the second material layer 25 may have a thickness of less than about 10 nanometers. Alternatively, the second material layer 25 may have a thickness of less than about 100 nanometers.

A first material layer 22 may be deposited over the second material layer 25. The distance $D_1$, separating individual quantum dots 11 in each pair of quantum dots 11 shown in FIG. 1 may be, at least partially, a function of the thickness of the first material layer 25. The first material layer 22 may have a thickness in a range from about 1 nanometer to about 100 nanometers.

A second material layer 26 may be deposited over the first material layer 22. The thickness of one individual quantum dot 11 in each pair of quantum dots 11 shown in FIG. 1 in the X direction may be, at least partially, a function of the thickness of the second material layer 26. Therefore, the second material layer 26 may have a thickness of less than about 10 nanometers. Alternatively, the second material layer 26 may have a thickness of less than about 100 nanometers.

A first material layer 23 may be deposited over the second material layer 26. The thickness of the first material layer 21 is not critical and may be greater than about 10 nanometers. For example, the first material layer 21 may be several microns thick.

Each of the first material layers 20 and the second material layers 24 may be deposited by, for example, physical vapor deposition techniques, chemical vapor deposition techniques, or any other technique known in the art suitable for depositing thin layers of material. The superlattice structure 18 may include from one to thousands, or even millions, of second material layers 24. In addition, the thickness of each material layer may be equal to or may differ from the thickness of other material layers.

In this configuration, each of the first material layers 20 and the second material layers 24 together may form a stack of material layers having a surface 28 that is substantially parallel to the surface 30 of the superlattice substrate, as shown in FIG. 2A. The superlattice structure 18 may be cleaved along a plane 36 that is substantially perpendicular to the major surface 28 of the stack of material layers. As shown in FIG. 2B, cleaving the stack of material layers along plane 36 may expose each of the first material layers 20 and the second material layers 24 along a stamping surface 29 that is substantially parallel to the plane 36 on at least a portion of the superlattice structure 18.

The exposed surface of each of the first material layers 20 and the second material layers 24 may be etched at the stamping surface 29 with an etchant that etches the first material layers 20 at a greater rate than the second material layers 24. For example, hydrofluoric acid may be used to etch the exposed surface of each of the first material layers 20 and the second material layers 24 at the stamping surface 29. Alternatively, other wet or dry chemical etching methods may be used to etch the exposed surface of each of the material layers at the stamping surface 29. As shown in FIG. 2C, etching the stamping surface 29 with such an etchant may form a first nanostrip 40 that protrudes beyond the stamping surface 29 of the superlattice structure 18 from a portion of the second material layer 25, and a second nanostrip 42 that protrudes beyond the stamping surface 29 of the superlattice structure 18 from a portion of the second material layer 26.

The distance that the first nanostrip 40 and the second nanostrip 42 protrude from the adjacent first material layers 20 at the stamping surface 29 may be depend on the etch rate for the etchant with respect to the materials and the amount of time the etchant is allowed to etch the first material layers 20 and the second material layers 24 at the stamping surface 29. This distance that the quantum dots 11 (shown in FIG. 1) extend from the surface 12 of the substrate 14 in the Z direction may be, in part, a function of the distance that the first nanostrip 40 and the second nanostrip 42 protrude from the adjacent first material layers 20 at the stamping surface 29 (shown in FIG. 2C).

Figure 3B:
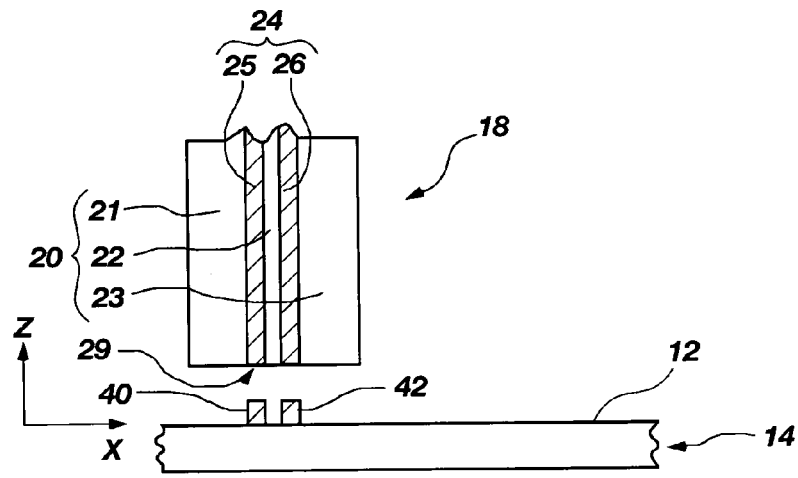
Figure 3C:
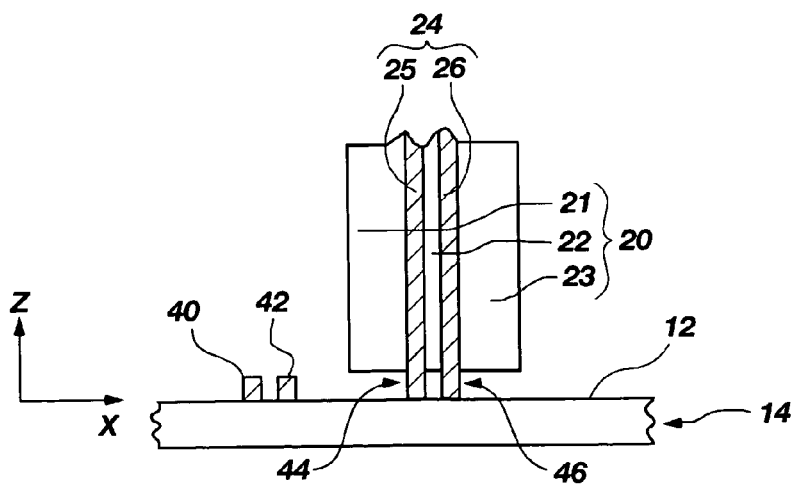
Figure 3D:
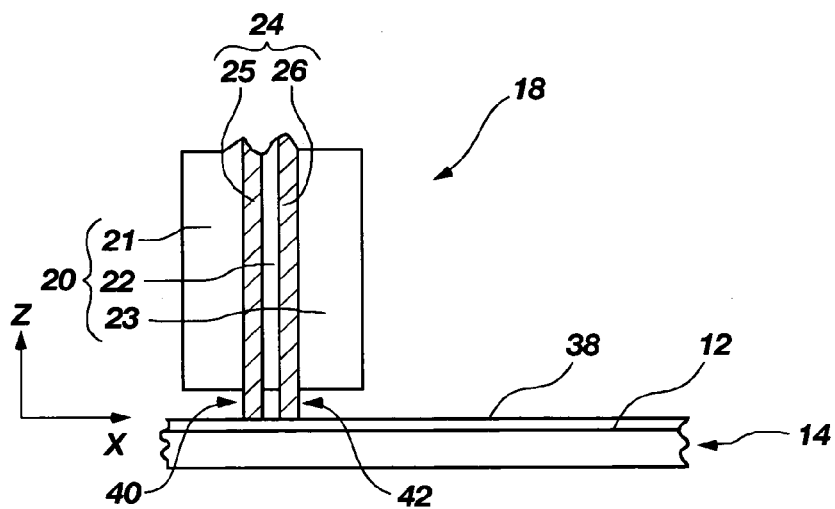
Figure 4:
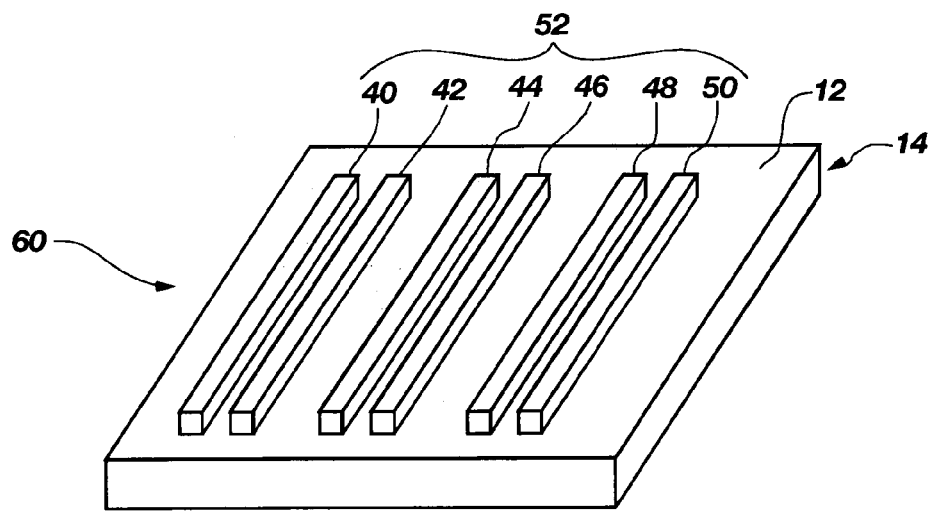
FIG. 4 is a perspective view of a representative intermediate structure that can be used to form the plurality of quantum dots shown in FIG. 1.

The superlattice structure 18 then may be used to form an intermediate structure 60 shown in FIG. 4 that can be used to form the plurality of quantum dots 11 shown in FIG. 1. An exemplary method for forming the intermediate structure 60 shown in FIG. 4 can be described in detail with reference to FIGS. 3A-3D.

As shown in FIG. 3A, the surface 12 of the substrate 14 may be stamped with the stamping surface 29 of the superlattice structure 18 at a selected region on the surface 12 such that the first nanostrip 40 and the second nanostrip 42 are pressed against the surface 12 of the substrate 14. At least a portion of each of the first nanostrip 40 and the second nanostrip 42 may be transferred from the superlattice structure 18 to the surface 12 of the substrate 14 as shown in FIG. 3B.

The exposed surface of each of the first material layers 20 and the second material layers 24 at the stamping surface 29 again may be etched with an etchant that etches the first material layers 20 at a greater rate than the second material layers 24 to form a third nanostrip 44 and a fourth nanostrip 46 that protrude from the stamping surface 29 of the superlattice structure 18. An additional selected region on the surface 12 of the substrate 14 may be stamped with the stamping surface 29 of the superlattice structure 18 at surface 12 such that the third nanostrip 44 and the fourth nanostrip 46 are pressed against the surface 12 of the substrate 14, as shown in FIG. 3C. At least a portion of each of the third nanostrip 44 and the fourth nanostrip 46 may be transferred from the superlattice structure 18 to the surface 12 of the substrate 14. This process again may be repeated to provide a fifth nanostrip 48 and a sixth nanostrip 50 at another selected region on the surface 12 of the substrate 14 to form the intermediate structure 60 shown in FIG. 4. The process described above in reference to FIGS. 3A-3C may be repeated a number of times to provide a selected number of nanostrips on the surface of a substrate.

Referring to FIG. 3D, in a representative embodiment, the surface 12 of the substrate 14 may be treated to facilitate adhesion of at least a portion of each of the nanostrips to the surface 12 of the substrate 14. For example, a thin layer of curable epoxy film 38 may be applied to the surface 12 of the substrate 14. The surface 12 of the substrate 14 then may be stamped with the stamping surface 29 of the superlattice structure 18 such that the first nanostrip 40 and the second nanostrip 42 are pressed against the substrate 14 and are in contact with the curable epoxy film 38. The curable epoxy film 38 may be cured while the first nanostrip 40 and the second nanostrip 42 are pressed against the substrate 14 to adhere at least a portion of the first nanostrip 40 and the second nanostrip 42 to the surface 12 of the substrate 14. In alternative methods, the surface chemistry of the surface 12 of the substrate 14 may be modified to facilitate adhesion instead of depositing an additional layer of material to facilitate adhesion.

As seen in FIG. 4, the intermediate structure 60 may include a plurality of nanostrips 52 disposed on the surface 12 of the substrate 14. The plurality of nanostrips 52 may include three pairs of substantially parallel nanostrips. It should be understood that if the superlattice structure 18 includes only one second material layer 24, only one nanostrip may be transferred to the surface 12 of the substrate 14 each time the surface 12 is stamped with the superlattice structure 18. Furthermore, if the superlattice structure 18 includes thousands of second material layers 24, thousands of nanostrips may be transferred to the surface 12 of the substrate 14 each time the surface 12 is stamped with the superlattice structure 18. Therefore, the ability to form a large number and/or configurations of nanostrips 52 quickly may be facilitated by providing a large number of second material layers 24.

The methods disclosed herein may be used to form intermediate structures having other configurations of nanostrips 52. For example, the superlattice structure 18 may be moved relative to the substrate 14 by varying distances between successive stampings to provide nanostrips 52 that are separated from one another by various distances on the surface 12 of the substrate 14. In addition, the superlattice structure 18 may be rotated relative to the substrate 14 between successive stampings to provide nanostrips that are oriented at an angle relative to one another on the surface 12 of the substrate 14. In this manner, various configurations of nanostrips 52 may be provided.

An exemplary method for forming the quantum dots 11 shown in FIG. 1 from the intermediate structure 60 shown in FIG. 4 may be described with reference to FIGS. 5A-5C. The exemplary method includes the removal of at least a portion of each nanostrip 52 from the surface 12 of the substrate 14.

Figure 5A:
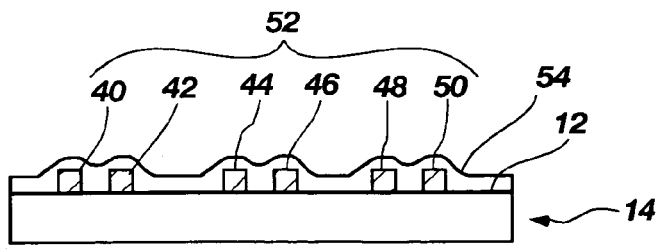
FIGS. 5A-5C illustrate a representative method for forming the plurality of quantum dots shown in FIG. 1 from the intermediate structure shown in FIG. 4.
Figure 5B:
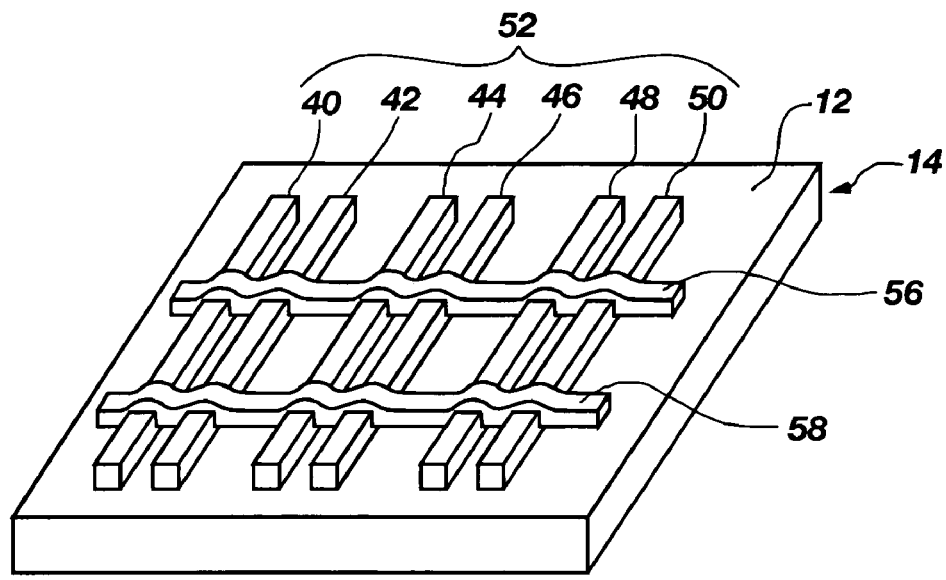

The surface 12 of the substrate 14 and each of the nanostrips 52 may be covered with a mask material 54, as shown in FIG. 5A. At least a portion of the mask material 54 may be removed to provide a pattern in the mask material that covers at least a portion of at least one of the nanostrips 52. For example, a portion of the mask material 54 may be removed by electron beam lithographic techniques known in the art to provide a pattern in the mask that includes a first nanostrip of mask material 56 and a second nanostrip of mask material 58 that each overlie at least a portion of at least one nanostrip 52, as shown in FIG. 5B. The first nanostrip of mask material 56 and the second nanostrip of mask material 58 may overlie a portion of each of the nanostrips 52 and may be oriented substantially perpendicular relative to the nanostrips 52, as shown in FIG. 5B. Alternatively, many other mask patterns that cover at least a portion of at least one nanostrip 52 may be formed in the mask material.

Figure 5C:
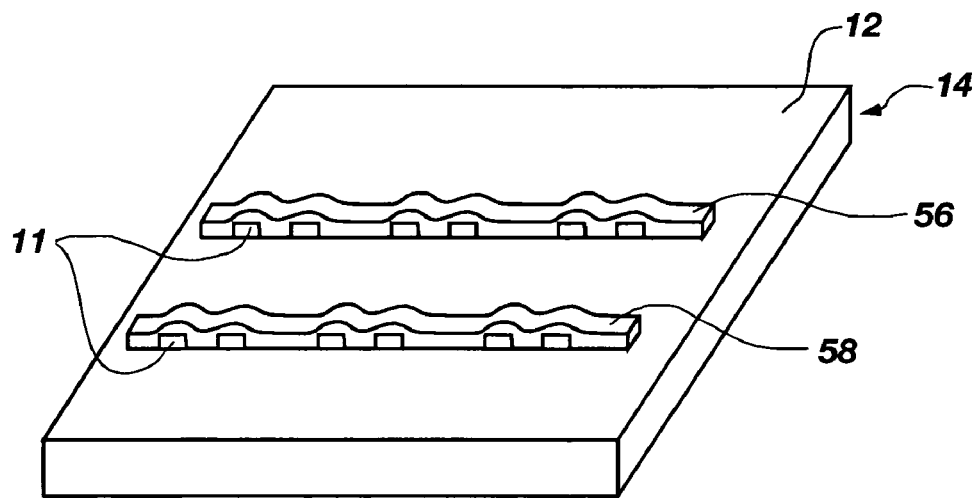

The exposed portions of each nanostrip 52 that are not covered by the first nanostrip of mask material 56 or the second nanostrip of mask material 58 may be removed to provide the structure shown in FIG. 5C. The exposed portions of each nanostrip 52 may be removed by, for example, etching the exposed portions of each nanostrip 52 with a selective etchant that will etch the exposed portions of each nanostrip 52 at a rate that is greater than the rate at which the etchant etches the first nanostrip of mask material 56 and the second nanostrip of mask material 58. Depending on the selective etchant used, the etchant may not etch the mask material at all.

In FIG. 5C, quantum dots 11 have been formed from the portions of each nanostrip 52 covered by the first nanostrip of mask material 56 or the second nanostrip of mask material 58 upon removing the exposed portions of each nanostrip 52. The first nanostrip of mask material 56 and the second nanostrip of mask material 58 may be removed from the quantum dots 11 to provide the structure shown in FIG. 1 by etching the first nanostrip of mask material 56 and the second nanostrip of mask material 58 with a selective etchant that will etch the mask material at a rate that is greater than the rate at which the etchant etches the quantum dots 11. Depending on the selective etchant used, the etchant may not etch the quantum dots at all.

Various methods other than electron beam lithographic techniques may be used to remove at least a portion of the mask material 54 to provide the pattern therein. For example, nanoimprinting techniques may be used to remove at least a portion of the mask material 54 to provide the pattern therein. An exemplary nanoimprinting technique for removing at least a portion of the mask material 54 is described with reference to FIGS. 6A to FIG. 6E.

Figure 6A:
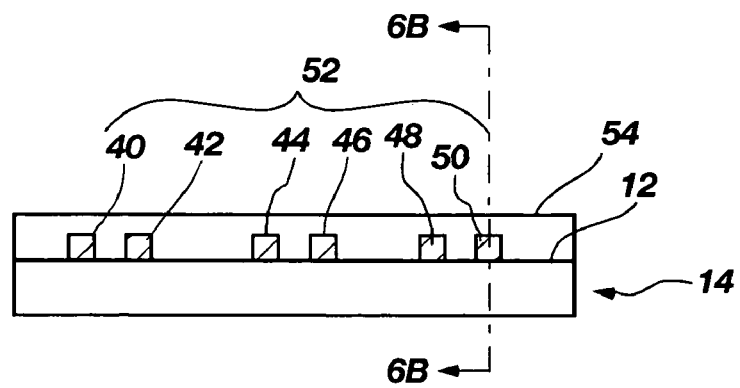
FIGS. 6A-6E illustrate an additional representative method for forming the plurality of quantum dots shown in FIG. 1 from the intermediate structure shown in FIG. 4.
Figure 6B:
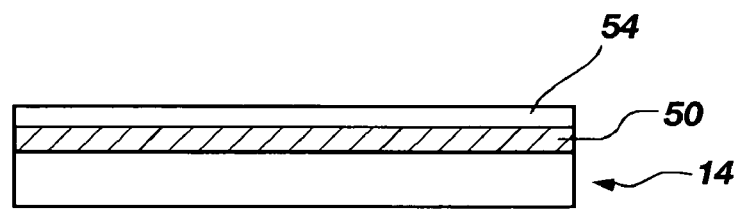

After at least one nanostrip 52 has been provided on the surface 12 of the substrate 14, the surface 12 of the substrate 14 and the at least one nanostrip 52 may be covered with a layer of mask material 54 as shown in FIGS. 6A and 6B. FIG. 6A is an end view illustrating an end of each nanostrip 52. FIG. 6B is a cross-sectional view taken along section line 6B-6B shown in FIG. 6A. The layer of mask material 54 may have an upper surface that is substantially planar. The mask material 54 may be, for example, a deformable thermoplastic material such as poly-methyl methacrylate (PMMA). Other deformable thermoplastic materials having physical properties suitable for use as the mask material 54 may also be used.

Figure 6C:
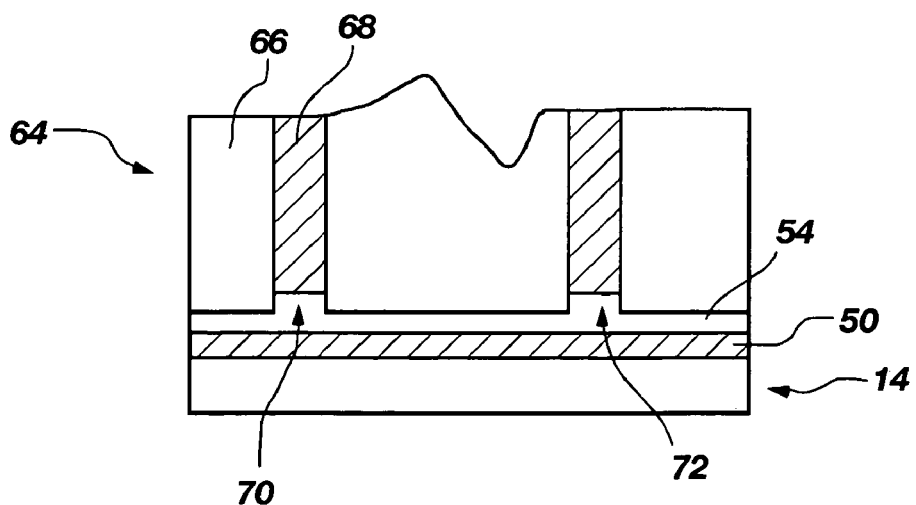
Figure 6D:
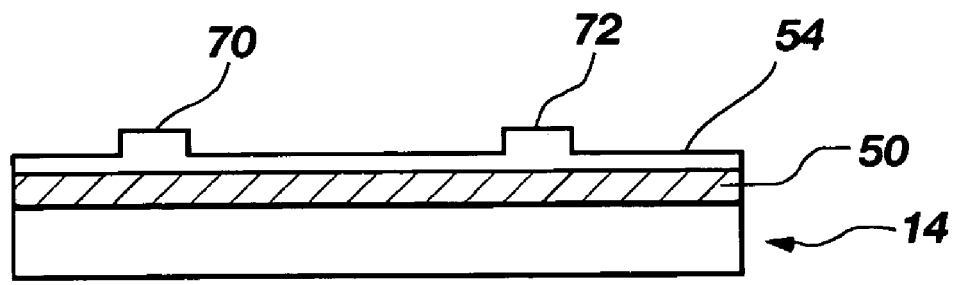

A nanoimprinting mold or platen 64 including a superlattice structure may be formed by methods substantially similar to those used to form the superlattice structure 18 previously described. FIG. 6C is a cross-sectional view like that of FIG. 6B illustrating the nanoimprinting mold 64 being used to form a first ridge 70 and a second ridge 72 in the mask material 54. As seen in FIG. 6C, the nanoimprinting mold 64 may include alternating layers of a first material 66 and a second material 68. An imprinting surface of the nanoimprinting mold 64 may be etched with an etchant that etches the second material 68 at a rate that is greater than the rate at which the etchant etches the first material 66. When the nanoimprinting surface of the nanoimprinting mold 64 is pressed against the mask material 54, as shown in FIG. 6C, the first ridge 70 and the second ridge 72 may be formed in the mask material 54 to form the structure shown in FIG. 6D. FIG. 6D is a cross-sectional view like that of FIG. 6B.

Alternatively, the nanoimprinting mold 64 may be formed so as to not include a superlattice structure. For example, the nanoimprinting mold may include a material such as silicon, and the nanoimprinting surface of the nanoimprinting mold 64 may be formed using, for example, electron or ion beam lithographic techniques.

Figure 6E:
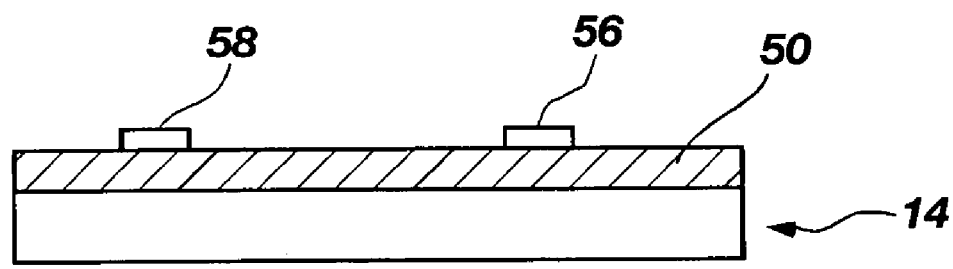

At least a portion of the mask material 54 may be removed to form the first nanostrip of mask material 56 and the second nanostrip of mask material 58, as shown in FIG. 6E, which is a cross-sectional view like that of FIGS. 6B and 6D. The portion of the mask material 54 may be removed by, for example, etching the mask material 54. The structure shown in cross-sectional view in FIG. 6E is substantially similar to the structure shown in the perspective view of FIG. 5B. The quantum dots 11 shown in FIG. 1 may be formed from the structure shown in FIG. 6E in the same manner as that previously described with reference to FIGS. 5B and 5C.

In particular, the exposed portions of each nanostrip 52 (FIG. 6A) that are not covered by the first nanostrip of mask material 56 or the second nanostrip of mask material 58 may be removed to form the quantum dots 11 by, for example, etching the exposed portions of each nanostrip 52 with a selective etchant. The first nanostrip of mask material 56 and the second nanostrip of mask material 58 may then be removed from the quantum dots 11 to provide the structure shown in FIG. 1 by etching the first nanostrip of mask material 56 and the second nanostrip of mask material 58 with a selective etchant.

Various configurations of quantum dots, which may include pairs, trios, quartets, quintets, etc. of quantum dots, may be provided using the methods described herein. These methods also allow for the mass production of quantum dots having well controlled size, shape, and separations therebetween. Furthermore, it should be understood that the methods described herein also may be used to form nanoparticles larger in size than quantum dots on the surface of a substrate having well controlled size, shape, and separations therebetween.

The structure 10 shown in FIG. 1 may be configured as a NERS-active structure and may be used to perform NERS where the second material layers 24 of the superlattice structure 18 (shown in FIGS. 2A-2C), and the resulting quantum dots 11, include a NERS-active material. The substrate 14 may be formed from an electrically insulating material. The intensity of Raman scattered radiation that is scattered by an analyte may be significantly enhanced if the analyte is disposed between or proximate to the quantum dots 11 (shown in FIG. 1) that include a NERS-active material such as, for example, gold, silver, copper, platinum, or palladium.

Figure 7:
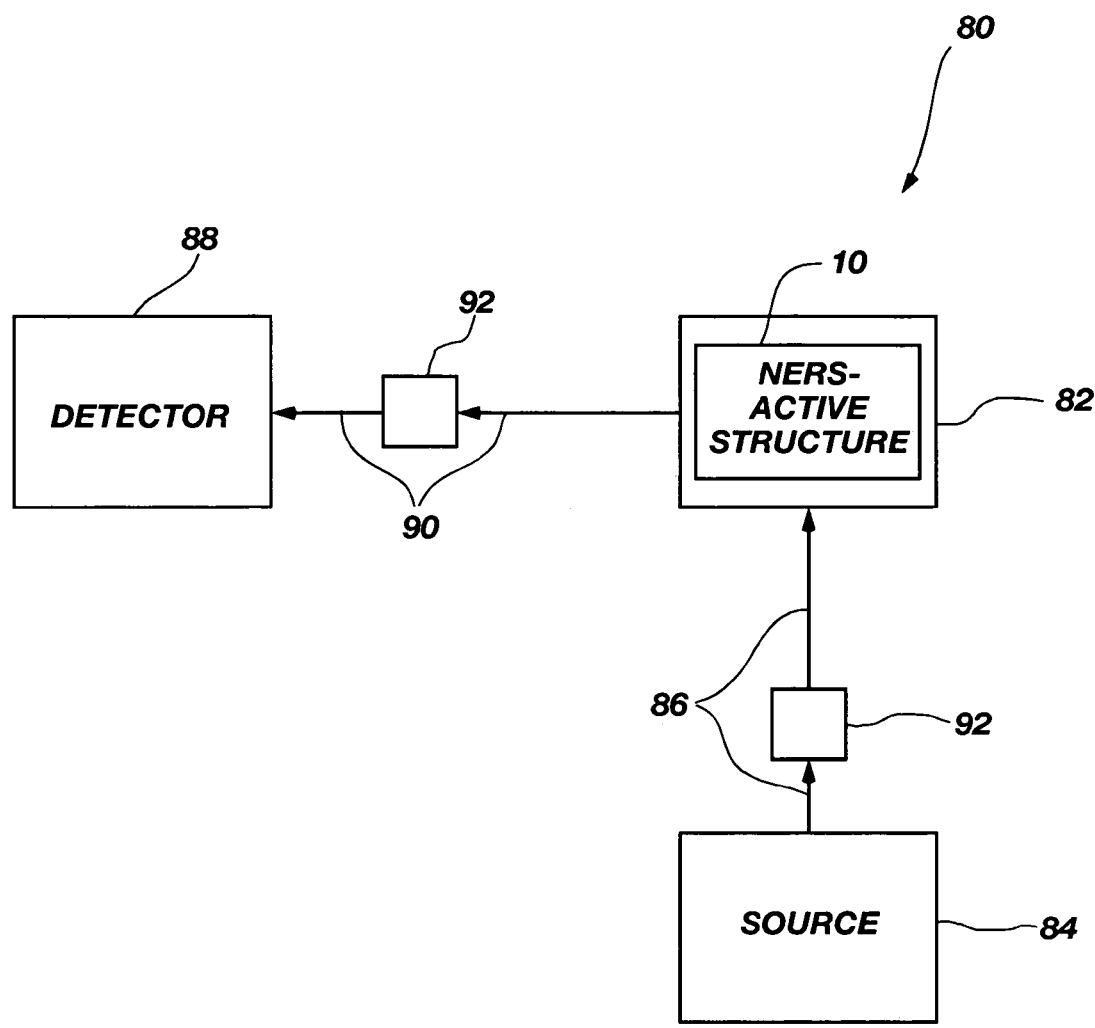
FIG. 7 is a schematic diagram of a representative NERS system that can be used with the NERS-active structure shown in FIG. 1 to perform NERS.

The NERS-active structure 10 including quantum dots 11 shown in FIG. 1 can be employed in conjunction with a NERS systems to perform NERS on an analyte. An exemplary NERS system 80 is illustrated schematically in FIG. 7. The NERS system 80 may include an analyte stage 82 for holding a NERS-active structure and an analyte. The NERS system 80 also may include a radiation source 84 for providing incident radiation 86, and a detector 88 for detecting Raman scattered radiation 90. The NERS system 80 also may include various optical components 92 such as, for example, lenses and filters positioned between the radiation source 84 and the analyte stage 82, and between the analyte stage 82 and the detector 88.

The radiation source 84 may include any suitable source for emitting radiation at the desired wavelength and may be capable of emitting a tunable wavelength of radiation. For example, commercially available semiconductor lasers, helium-neon lasers, carbon dioxide lasers, radiation emitting diodes, incandescent lamps, and many other known radiation emitting sources may be used as the radiation source 84. The wavelengths that are emitted by the radiation source 84 may be any suitable wavelength for performing NERS on the analyte. An exemplary range of wavelengths that may be emitted by the radiation source 84 includes wavelengths between about 350 nanometers and about 1000 nanometers.

The detector 88 may receive and detect the Raman scattered radiation 90 generated by Raman scattered photons that are scattered by the analyte. The detector 88 may include a device for determining the wavelength of the Raman scattered radiation 90, such as, for example, a monochromator, and a device for determining the intensity of the Raman scattered radiation 90, such as, for example, a photomultiplier. Typically, the Raman scattered radiation 90 is scattered in all directions relative to the analyte stage 82. Thus, the position of the detector 88 relative to the analyte stage 82 may not be particularly important. However, the detector 88 may be positioned at, for example, an angle of approximately 90° relative to the direction of the incident radiation 86 to minimize the intensity of any incident radiation 86 that impinges unintentionally on the detector 88.

Optical components 92 may be positioned between the source 84 and the analyte stage 82 to collimate, filter, or focus the incident radiation 86 before the incident radiation 86 impinges on the analyte stage 82 and the NERS-active structure. Optical components 92 positioned between the analyte stage 82 and the detector 88 may be used to collimate, filter, or focus the Raman scattered radiation 90. For example, a filter or a plurality of filters may be employed to prevent radiation at wavelengths corresponding to the incident radiation 86 from impinging on the detector 88, thus allowing primarily only the Raman scattered radiation 90 to be received by the detector 88.

To perform NERS using the NERS system 80, the analyte may be provided adjacent the NERS-active structure. The NERS-active structure and the analyte may then be irradiated with incident radiation 86 provided by the source 84. Raman scattered radiation 90 scattered by the analyte is detected by the detector 88. The NERS-active structure of the analyte stage 82 may enhance the intensity of the Raman scattered radiation 90.

The wavelengths and corresponding intensity of the Raman scattered radiation 90 may be determined and used to identify and provide information about the analyte.

The methods for forming quantum dots, methods for forming NERS-active structures including quantum dots, and the NERS-systems disclosed herein allow for improved nano-enhanced Raman spectroscopy techniques. The performance of molecular sensors, nanoscale electronics, optoelectronics, and other devices employing the Raman effect can be improved by using NERS-active structures, or structures including quantum dots fabricated as described herein.

Although the foregoing description contains many specifics, these are not to be construed as limiting the scope of the present invention, but merely as providing certain exemplary embodiments. Similarly, other embodiments of the invention can be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. A method for forming at least two quantum dots comprising:
   forming a superlattice structure comprising:
      providing a superlattice substrate;
      forming a plurality of alternating layers of a first material and a second material on the superlattice substrate to form a stack having a major surface parallel to that of the superlattice substrate, the second material differing from the first material;
      cleaving the stack normal to the major surface to expose the plurality of alternating layers; and
      etching the exposed plurality of alternating layers using an etchant that etches the first material at a greater rate than the second material to form at least one nanostrip comprising the second material, the at least one nanostrip protruding from the stack;
   providing a quantum dot substrate;
   transferring the at least one nanostrip comprising the second material from the superlattice structure to the quantum dot substrate; and
   removing at least a portion of the at least one nanostrip from the quantum dot substrate.

2. The method of claim 1, wherein transferring the at least one nanostrip comprises stamping the quantum dot substrate with the superlattice structure.

3. The method of claim 1, wherein removing at least a portion of the at least one nanostrip comprises:
applying a mask material over the at least one nanostrip and the quantum dot substrate;
removing at least a portion of the mask material to expose at least a portion of the at least one nanostrip;
removing at least a portion of the exposed portion of the at least one nanostrip; and
removing the remaining mask material from the remaining portion of the at least one nanostrip and the quantum dot substrate.

4. The method of claim 1, wherein the second material comprises a metal.

5. The method of claim 1, wherein transferring the at least one nanostrip comprises transferring the at least one nanostrip comprising the second material to a first region on a surface of the quantum dot substrate, further comprising:
re-etching the exposed plurality of alternating layers of the superlattice structure to form an additional at least one nanostrip comprising the second material;
transferring the additional at least one nanostrip comprising the second material to a second region on the surface of the quantum dot substrate;
continuing to re-etch the exposed plurality of alternating layers of the superlattice structure and to transfer nanostrips comprising the second material to the quantum dot substrate as necessary to provide a chosen number of nanostrips comprising the second material on the surface of the quantum dot substrate; and
removing at least a portion of the chosen number of nanostrips comprising the second material from the quantum dot substrate.

6. The method of claim 2, wherein transferring the at least one nanostrip further comprises treating the quantum dot substrate to facilitate adhesion of the at least one nanostrip to the quantum dot substrate.

7. The method of claim 3, wherein removing at least a portion of the mask material to expose at least a portion of the at least one nanostrip comprises using electron-beam lithography to remove at least a portion of the mask material.

8. The method of claim 3, wherein removing at least a portion of the mask material to expose at least a portion of the at least one nanostrip comprises:
stamping the mask material with a nanoimprinting mold; and
etching the mask material to remove at least a portion of the mask material.

9. The method of claim 6, wherein treating the quantum dot substrate comprises applying a layer of curable epoxy film to a surface of the quantum dot substrate prior to stamping the quantum dot substrate with the superlattice structure, and wherein transferring the at least one nanostrip further comprises curing the curable epoxy film to adhere the at least one nanostrip to the quantum dot substrate.

10. The method of claim 8, wherein the nanoimprinting mold is formed from a superlattice structure.

11. The method of claim 8, wherein providing a nanoimprinting mold comprises:
providing a mold structure; and
forming a nanoimprinting surface in a surface of the mold structure using electron-beam lithography.

12. A method for forming a NERS-active structure comprising:
forming a superlattice structure comprising:
providing a superlattice substrate;
forming a plurality of alternating layers of a first material and a second material on the superlattice substrate to form a stack having a major surface parallel to that of the superlattice substrate, the second material comprising a NERS-active material, the first material differing from the second material;
cleaving the stack normal to the major surface to expose the plurality of alternating layers; and
etching the exposed plurality of alternating layers using an etchant that etches the first material at a greater rate than the second material to form at least one nanostrip comprising the NERS-active material, the at least one nanostrip protruding from the stack;
providing a NERS-active structure substrate comprising an electrically insulating material;
transferring the at least one nanostrip comprising the NERS-active material from the superlattice structure to a surface of the NERS-active structure substrate; and
removing at least a portion of the at least one nanostrip comprising the NERS-active material from the NERS-active structure substrate to provide at least two quantum dots comprising the NERS-active material on the surface of the NERS-active structure substrate.

13. The method of claim 12, wherein the NERS-active material comprises gold, silver, or copper.

14. The method of claim 12, wherein transferring the at least one nanostrip comprises stamping the surface of the NERS-active structure substrate with the superlattice structure.

15. The method of claim 12, wherein removing at least a portion of the at least one nanostrip comprises:
applying a mask material over the at least one nanostrip and the surface of the NERS-active structure substrate;
removing at least a portion of the mask material to expose at least a portion of the at least one nanostrip;
removing at least a portion of the exposed portion of the at least one nanostrip; and
removing the remaining mask material from the remaining portion of the at least one nanostrip and the surface of the NERS-active structure substrate.

16. The method of claim 14, wherein transferring the at least one nanostrip further comprises treating the surface of the NERS-active structure substrate to facilitate adhesion of the at least one nanostrip to the surface of the NERS-active structure substrate.

17. The method of claim 15, wherein removing at least a portion of the mask material to expose at least a portion of the at least one nanostrip comprises using electron beam lithography to remove the at least a portion of the mask material.

18. The method of claim 15, wherein removing at least a portion of the mask material to expose at least a portion of the at least one nanostrip comprises:
providing a nanoimprinting mold;
stamping the mask material with the nanoimprinting mold; and
etching the mask material to remove at least a portion of the mask material.

19. The method of claim 16, wherein treating the surface of the NERS-active structure substrate comprises applying a layer of curable epoxy film to the surface of the NERS-active structure substrate prior to stamping the surface of the NERS-active structure substrate with the superlattice structure, and wherein transferring the at least one nanostrip further comprises curing the curable epoxy film to adhere the at least one nanostrip to the surface of the NERS-active structure substrate.

20. A method for performing NERS comprising:
providing a NERS-active structure comprising:
  forming a superlattice structure comprising:
    providing a superlattice substrate;
    forming a plurality of alternating layers of a first material and a second material on the superlattice substrate to form a stack having a major surface parallel to that of the superlattice substrate, the second material comprising a NERS-active material, the first material differing from the second material;
    cleaving the stack normal to its major surface to expose the plurality of alternating layers; and
    etching the exposed plurality of alternating layers using an etchant that etches the first material at a greater rate than the NERS-active material to form at least one nanostrip comprising the NERS-active material, the at least one nanostrip protruding from the stack;
  providing a NERS-active structure substrate comprising an electrically insulating material;
  transferring the at least one nanostrip comprising the NERS-active material to a surface of the NERS-active structure substrate; and
  removing at least a portion of the at least one nanostrip comprising NERS-active material from the surface of the NERS-active structure substrate to provide at least two quantum dots comprising the NERS-active material on the surface of the NERS-active structure substrate;
providing an analyte proximate the at least two quantum dots comprising the NERS-active material;
irradiating the analyte and the at least two quantum dots comprising the NERS-active material; and
detecting Raman scattered radiation scattered by the analyte.

* * * * *